(12) United States Patent
Giri et al.

(10) Patent No.: US 7,313,945 B2
(45) Date of Patent: Jan. 1, 2008

(54) CANTILEVERS FOR SENSING FLUID PROPERTIES

(75) Inventors: Manish Giri, Corvallis, OR (US); Mark Sanders Taylor, Corvallis, OR (US); Sriram Ramamoorthi, Corvallis, OR (US); Jeremy Harlan Donaldson, Corvallis, OR (US); Joshua Yu, Corvallis, OR (US); Mark D. Johnson, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 111 days.

(21) Appl. No.: 11/264,652

(22) Filed: Oct. 31, 2005

(65) Prior Publication Data

US 2007/0095129 A1    May 3, 2007

(51) Int. Cl.
*G01N 11/00* (2006.01)
(52) U.S. Cl. ...................................................... 73/53.1
(58) Field of Classification Search ............... 73/53.01, 73/54.01, 23.2
See application file for complete search history.

(56) References Cited

U.S. PATENT DOCUMENTS

| | | | |
|---|---|---|---|
| 5,659,195 A * | 8/1997 | Kaiser et al. ............... 257/415 |
| 5,955,659 A * | 9/1999 | Gupta et al. ................ 73/54.01 |
| 6,289,717 B1 | 9/2001 | Thundat et al. .............. 73/23.2 |
| 6,523,392 B2 | 2/2003 | Porter et al. ................ 73/24.01 |
| 6,631,648 B2 | 10/2003 | Lal et al. .................. 73/861.71 |
| 6,854,317 B2 | 2/2005 | Porter et al. ................ 73/31.05 |
| 6,904,786 B2 | 6/2005 | Matsiev et al. ............. 73/24.06 |
| 6,948,800 B2 | 9/2005 | Cabal et al. ................... 347/54 |
| 2003/0062193 A1* | 4/2003 | Thaysen et al. ............. 174/255 |
| 2003/0154771 A1* | 8/2003 | de Charmoy Grey et al. .......................... 73/53.01 |
| 2006/0075803 A1* | 4/2006 | Boisen et al. ............... 73/31.06 |

* cited by examiner

*Primary Examiner*—Hezron Williams
*Assistant Examiner*—Tamiko Bellamy

(57) ABSTRACT

A system for sensing a property of a fluid comprises a fluid channel operable to receive the fluid therein, a flexible arm having a free end positioned within at least a portion of the fluid channel, a fluid actuator disposed sufficiently close to the flexible arm such that actuation of the fluid actuator induces movement of the flexible arm when the fluid is present, and a deflection sensing system operable to quantifiably detect movement of the flexible arm.

30 Claims, 4 Drawing Sheets

US 7,313,945 B2

CANTILEVERS FOR SENSING FLUID PROPERTIES

BACKGROUND OF THE INVENTION

Micro-cantilever sensing systems have become popular tools for detecting properties of various fluids, including for use in detecting the presence of analytes in a particular fluid. Such micro-cantilever sensing systems are generally capable of measuring nanoscale deflections, nanomechanical resonances, and, in some cases, Q-factors of micro-cantilevers. In general, micro-cantilever systems utilize the concept that physical, chemical, or biological stimuli can affect the mechanical characteristics of a micro-cantilever in such a way that the resulting change can be measured using optical, electronic, and other sensing devices. Thus, by measuring a given physical aspect of a micro-cantilever, such as magnitude of deflection or vibratory frequency, some physical, chemical or biological aspect of the fluid in which the micro-cantilever is disposed can be detected or monitored.

In some exemplary cases, one side (or sometimes, both sides) of a micro-cantilever beam is "functionalized," e.g. treated to absorb or react with a particular analyte in a fluid, such that the absorption or reaction causes the behavior of the micro-cantilever within the fluid to change. Generally, the absorption or reaction causes an increase in mass of the micro-cantilever, which results in some change in physical response of the cantilever. Monitoring this change in response of the micro-cantilever can indicate, for example, the presence or concentration of a particular analyte in the fluid at issue. Micro-cantilever systems can include both "static" systems, which generally measure cantilever deformation as a means of monitoring absorption or reaction with an analyte, and "dynamic" systems, which generally measure resonance frequency of the micro-cantilever to monitor absorption or reaction with an analyte.

In general, dynamic micro-cantilever systems are often more sensitive to minute changes in behavior of a micro-cantilever and are thus preferred in many applications over static micro-cantilevers. However, as the sensitivity of a dynamic micro-cantilever system often depends upon the quality factor (or "Q") of the micro-cantilever, dynamic systems do not often perform well in systems in which a fluid with a relatively high viscosity is used. This is due to the fact that a relatively high viscosity fluid will dampen the reaction of the micro-cantilever, thereby reducing the Q and the sensitivity of the cantilever. While some systems have attempted to compensate for this condition and utilize dynamic micro-cantilevers in liquids, such systems have required the use of sophisticated active feedback control systems to counter the highly damped signal.

DETAILED DESCRIPTION OF THE PREFERRED EMBODIMENT(S)

Figure 1A:
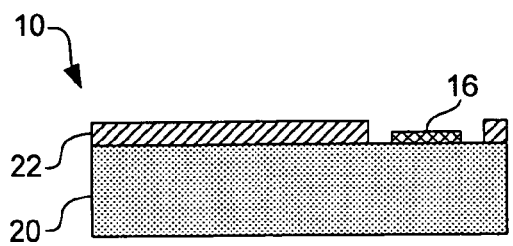
FIG. 1A through FIG. 1F are front, sectional schematic views of a cantilever system for detecting properties of a fluid in accordance with an exemplary embodiment of the invention, shown in sequential order through an exemplary method of forming the cantilever system.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used:

The singular forms "a," "an," and "the" include plural referents unless the context clearly dictates otherwise.

As used herein, the term "micro-cantilever" is to be understood to refer to flexible arms that include a width dimension (relative to a longitudinal axis of deflection) less than about 0.5 mm.

As used herein, the terms "microfluid" or "microfluids" are to be understood to refer to fluids manipulated in systems that confine the fluids within geometric channels, passages, or reservoirs having at least one dimension less than about 1 mm. Similarly, the terms "microfluidic channel," or "microchannel" are to be understood to refer to channels having at least one dimension less than about 1 mm.

As used herein, the term "fluid actuator" is to be understood to refer to a device that, when actuated while within or adjacent to a fluid, propagates differential pressure waves through the fluid that are sufficient to induce movement in a cantilever disposed nearby within the fluid.

As used herein, the term "acoustic actuator" is to be understood to refer to a device that, when actuated while within or adjacent a fluid, propagates acoustic waves through the fluid that are sufficient to induce movement in a cantilever disposed nearby within the fluid.

As used herein, the terms "functionalized" or "functional" are to be understood to refer to the result of a process that enables a substrate to selectively react with at least one component of a fluid when the substrate is disposed within the fluid. Substrates or surfaces of cantilevers can be functionalized, for example, with silane coupling agents having functional groups attached thereto that are configured to selectively bind to certain analytes within a fluid.

When referring to a "fluid," it is understood that solutions or dispersions are included. In other words, the presence of small molecules or dispersed particles in a liquid or gas is still considered to be a fluid in accordance with embodiments of the present invention.

In accordance with embodiments of the present invention, it has been recognized that it would be advantageous to develop a relatively simplistic, accurate, low-cost, and highly sensitive detection mechanism for determining properties of fluids and, in particular, properties of liquids. In accordance with one aspect of the invention, a system for sensing a property of a fluid is provided, including a fluid channel operable to receive the fluid therein. A flexible arm can have a free end positioned within at least a portion of the fluid channel. A fluid actuator can be disposed sufficiently close to the flexible arm such that actuation of the fluid actuator induces movement of the flexible arm when the fluid is present. A deflection sensing system can be operable to quantifiably detect movement of the flexible arm.

In accordance with another aspect of the invention, a method for forming a cantilever system for use in determining a property of a fluid is provided, including the steps of: forming a polymeric flexible arm; and disposing a fluid actuator proximate to and spaced from the polymeric flexible arm, wherein the polymeric flexible arm and the fluid actuator are sufficiently close in proximity that actuation of the fluid actuator in the presence of the fluid induces movement of the polymeric flexible arm.

In accordance with another aspect of the invention, a method for forming an integrated micro-electro-mechanical sensing system for use in a fluid is provided, including the steps of: forming a flexible arm of the sensing system, the flexible arm including at least two connector strips of electrically conducting material; and coupling an actuator to the flexible arm and to at least a portion of each of the two connector strips of electrically conducting material, the actuator operable to induce movement in the deflectable arm upon actuation of the actuator.

In accordance with another aspect of the invention, a system for sensing a property of a fluid is provided, including a fluid channel operable to receive the fluid therein. A flexible arm can have a free end positioned within at least a portion of the fluid channel. Means for actuating the fluid to induce movement of the flexible arm when the fluid is present can be disposed sufficiently close to the flexible arm to induce movement in the arm. Means for sensing deflection of the flexible arm to quantify movement of the flexible arm can be associated with the system.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 1B:
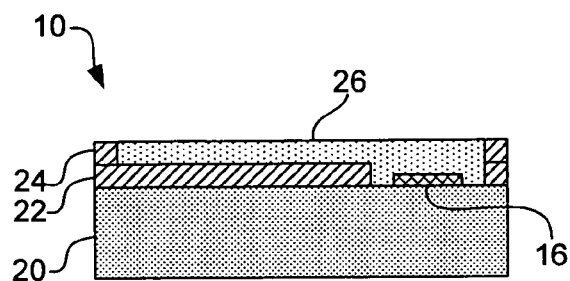
Figure 1C:
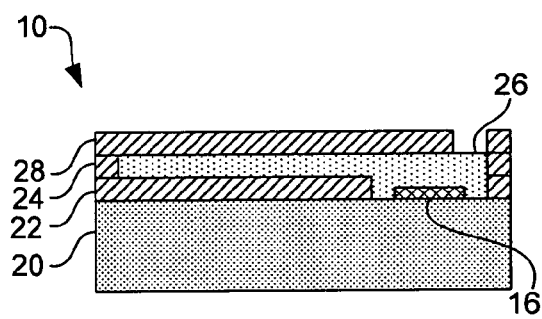
Figure 1D:
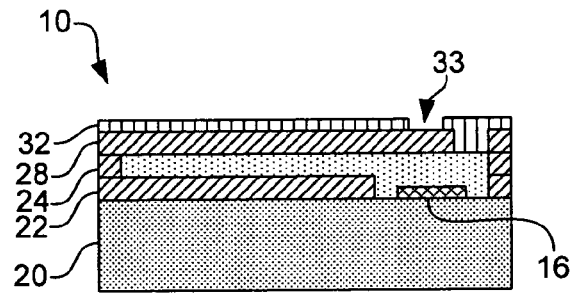
Figure 1E:
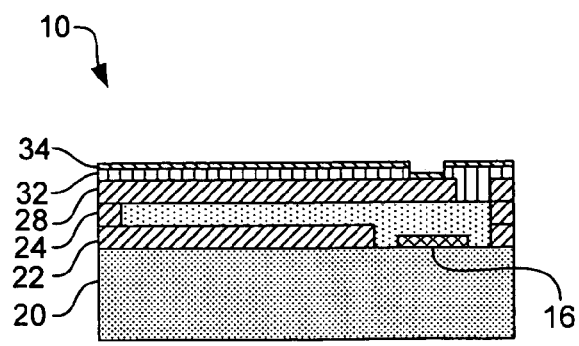
Figure 1F:
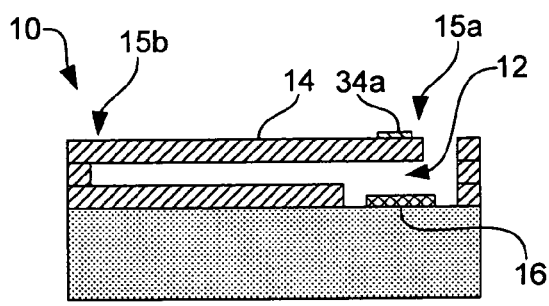

As shown generally in sectional view FIG. 1F, in one aspect of the invention, a system 10 for sensing a property of a fluid is provided. The system can generally include a fluid channel 12 that can be operable to receive a fluid (not shown in the figures) therein. A flexible arm 14 can include a free end 15a and a fixed end 15b that can cooperatively define a cantilever beam that can flex, deflect and/or oscillate at the free end. The free end can be positioned within at least a portion of the fluid channel, and is generally, although not always, completely submerged in a fluid body of which the fluid in the fluid channel comprises a portion. A fluid actuator 16 can be disposed sufficiently close to the flexible arm such that actuation of the fluid actuator induces movement of the flexible arm when the fluid is present. A deflection sensing system (not shown) can be in operable communication with the flexible arm and can be configured to quantifiably detect movement of the flexible arm.

The cantilever sensing system of the present invention can be used in a variety of applications and is particularly well suited to detect or monitor one or more physical properties of a fluid. The cantilever systems can be used to detect viscosity of a fluid, the presence of a particular analyte in a fluid, the concentration of one or more analytes in a fluid, etc. While not so required, the cantilever systems are generally operated in a fluid environment in dynamic mode, e.g., with the free end 15a of the cantilever or flexible arm 14 oscillating upwardly and downwardly while the frequency and/or magnitude of the movement are monitored with a suitable system. Deflection sensing systems suitable for measuring the frequency and/or magnitude of displacement of the flexible arm are not shown in the figures but are well known to those having skill in the relevant art and can include, without limitation, optical systems which direct one or more optical beams at the cantilever, strain measuring systems utilizing devices such as wheatstone bridge strain gauges, piezoelectric sensors, etc. One specific system includes a laser device having appropriate feedback capabilities. In one aspect of the invention (discussed in more detail below) the flexible arm includes a piezoelectric sensor incorporated into or onto the flexible arm to measure movement of the arm.

The fluid actuator 16 utilized with the present system can take a variety of forms, and in one embodiment the fluid actuator includes a resistor capable of generating a relatively high (e.g., on the order of $10^9$ K/s) temperature gradient between the resistor and the fluid adjacent the resistor. In this manner, actuation of the resistor results in rapid heating of the fluid adjacent the resistor, which in turn results in generation of at least one acoustic pressure wave that travels through the fluid and imparts or induces movement in the flexible arm 14. It has been found that resistors suitable for use in thermal ink-jet systems perform well as the fluid actuator through a range of fluid viscosities. Thus, in one aspect of the invention, the fluid actuator comprises a thermal ink-jet-type actuator.

In addition to thermal resistors, other types of fluid actuators can be utilized, including acoustic actuators that create pressure waves in the fluid adjacent the actuator, resulting in movement of the flexible arm 14. For example, it is contemplated that relatively small, high-energy acoustic transmitters can be utilized to propagate high-intensity shock waves through the fluid to induce movement in the flexible arm. In general, a variety of types of fluid actuators can be utilized, so long as actuation of the fluid actuator reliably induces or creates movement in the flexible arm.

The location of the fluid actuator 16 can vary depending upon the type of actuator used, the fluid in which the system is submerged, the physical property of the fluid that is to be measured, etc. In the embodiment of the invention illustrated in FIG. 1F, the actuator 16 is disposed proximate to, and spaced from, the flexible arm 14. In the embodiment illustrated in FIGS. 2K and 3, the actuator 16a is coupled to the flexible arm 14a itself. In either case, actuation of the actuator results in the generation of pressure waves within the fluid adjacent the actuator, causing the flexible arm to move. The characteristics of the movement of the flexible arm can then be used by the system to determine some property of the fluid within the fluid channel 12.

The cantilever sensing systems of the present invention are particularly well suited for use in liquids that have relatively high viscosities. Conventional cantilever sensing systems have encountered numerous problems when used in liquid environments due, in part, to the fact that the liquid dampens or retards the oscillatory motion of the flexible arm. For this reason, creating or sustaining predictable motion of the flexible arm has been difficult in the past. This problem is addressed by the present invention by disposing the fluid actuator 16, 16a on or near the flexible arm 14, 14a. Due to the proximity of the fluid actuator to the flexible arm, actuation of the fluid actuator can induce movement in the flexible arm sufficient to provide good analytic results from the cantilever, even in relatively high-viscosity fluids.

Operation and calibration of the cantilever system can vary according to the type of testing to be performed. However, in general, the cantilever system can be used to compare a particular "baseline" physical property of a fluid to a corresponding property of the same fluid (or a different fluid) at a later time. For example, the cantilever system can be used to measure the viscosity of a fluid by operating the actuator in a baseline fluid with a known viscosity and monitoring the magnitude and/or frequency response of the flexible arm within the baseline fluid. A second fluid (or the same fluid after undergoing a change in viscosity) can then be introduced into the fluid channel, and the actuator can be operated while monitoring the response of the flexible arm to determine the viscosity of the second fluid, based upon the change in response of the cantilever system.

In another testing regime, the flexible arm can be "functionalized" to chemically react with a particular analyte within a fluid. A fluid can then be introduced into the fluid chamber and, if the "normal" response of the flexible arm is known, any change in the response of the flexible arm can be attributed to the functionalized portion of the flexible arm reacting with the analyte in the fluid. In this manner, the presence of (and/or the concentration of) the analyte in the fluid can be detected. The change in the response of the flexible arm can be due to the absorption of molecules on the functionalized portion of the flexible arm, or to the loss of or change in molecules from the functionalized portion (e.g., the flexible arm can either become heavier or lighter due to the chemical reaction, resulting in a change in the magnitude and/or frequency of the oscillatory motion of the free end of the flexible arm). Functionalization of the flexible arm can be done in a number of manners known to those of ordinary skill in the art, including adsorption of materials onto a substrate, chemical attachment to a substrate, e.g., using silane coupling agents, etc.

Turning now to FIGS. 1A through 1F, an exemplary method of forming a cantilever system 10 in accordance with the present invention is shown. In this aspect of the invention, the process can begin in FIG. 1A by forming an optional fluidic confinement layer 22 upon a base material 20. A fluid actuator 16 can be disposed between sections of the fluidic confinement layer, e.g., in an opening in the confinement layer. As shown in FIG. 1B, a cantilever base layer 24 can be added, with a removable support material or layer 26 covering the remainder of the confinement layer and the fluid actuator. The removable support layer can be a wax or other material that is relatively easily removed from the remaining structure. In FIG. 1C, a cantilever layer 28 can be added over the removable support layer. In FIG. 1D, a release liner 32 can be added to all but a small section 33 of the cantilever layer and exposed portions of the removable support layer. In FIG. 1E, a functionalizing agent 34 can be added to the exposed upper portions of the system. In this step, the functionalizing agent will generally bond well to the portion 33 of the cantilever layer that did not receive the release liner. Finally, in FIG. 1F, a washing or removing agent (not shown), such as an aqueous base, can be used to remove the removable support layer and the release liner, leaving flexible arm 14 free to move at the free end 15a, and having a functionalized section or portion 34a defined thereon.

While the various layers of the above-described invention can be formed from a variety of materials, in one aspect of the invention, the flexible arm can be formed from a polymer, such as SU-8 polymeric material. The remaining portions of the cantilever system (that were not removed during the process of forming the cantilever system) can also be formed of SU-8, or another suitable material. The SU-8 utilized can be of a dry film type, or a liquid type, each of which includes its own distinct advantages as is known in the art.

Figure 2A:
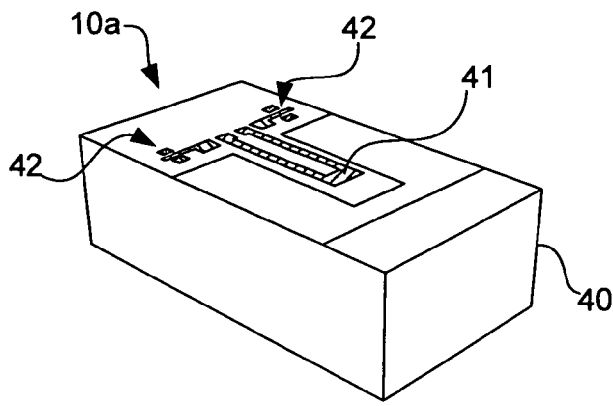
FIG. 2A through FIG. 2H and FIGS. 2J and 2K are schematic perspective views of another cantilever system for detecting properties of a fluid in accordance with an exemplary embodiment of the invention, shown in sequential order through an exemplary method of forming the cantilever system.
Figure 2B:
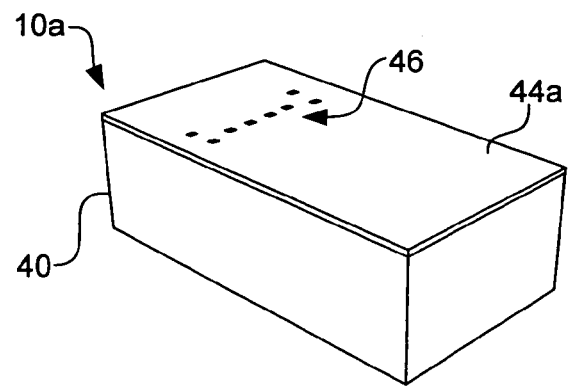
Figure 2C:
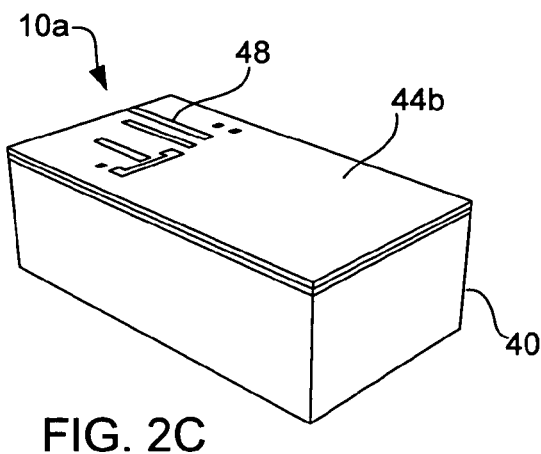
Figure 2D:
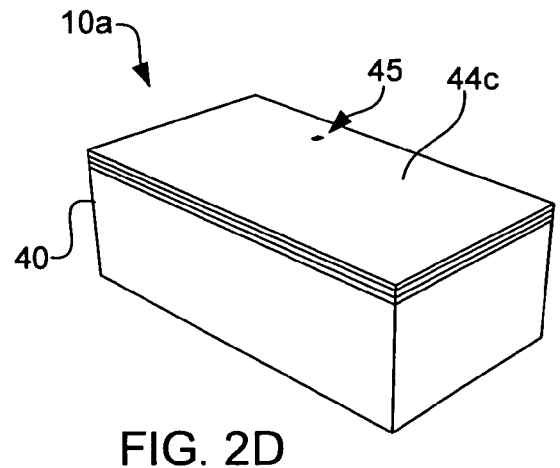
Figure 2E:
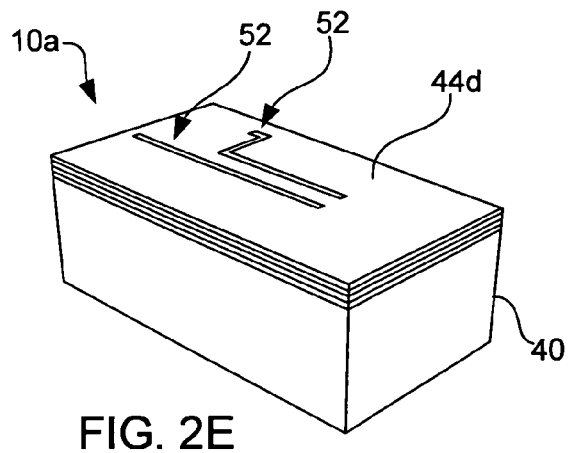
Figure 2F:
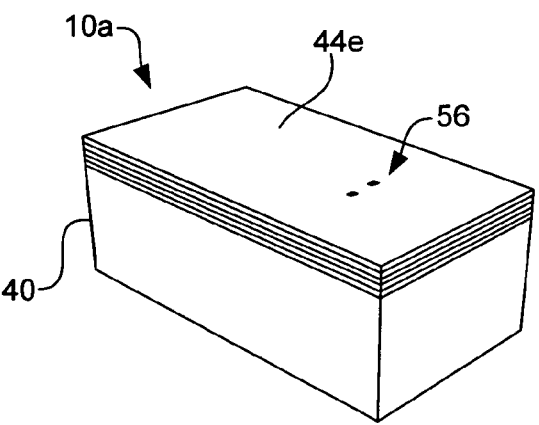
Figure 2G:
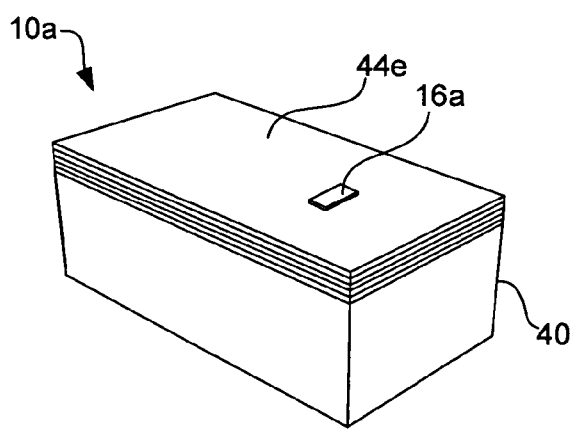
Figure 2H:
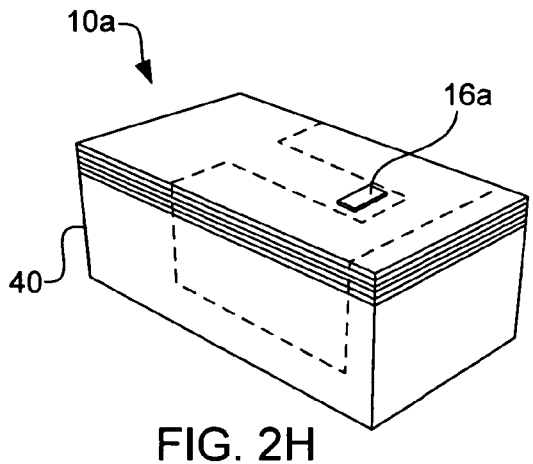
Figure 2J:
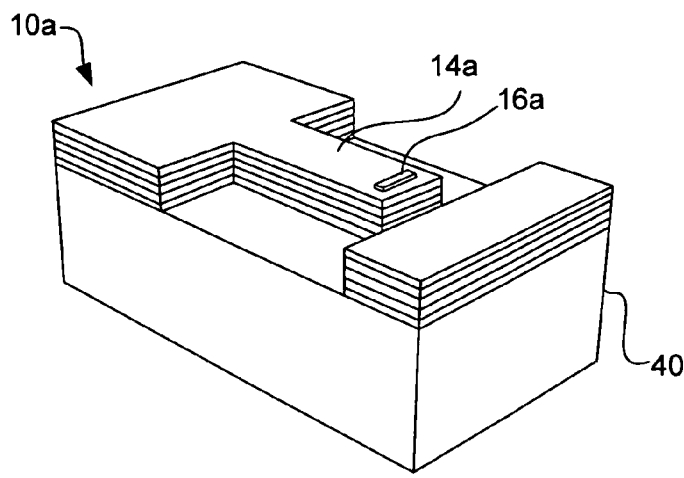
Figure 2K:
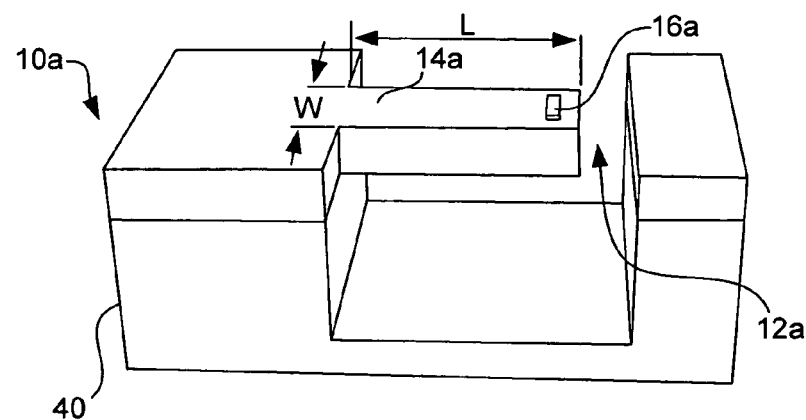
Figure 3:
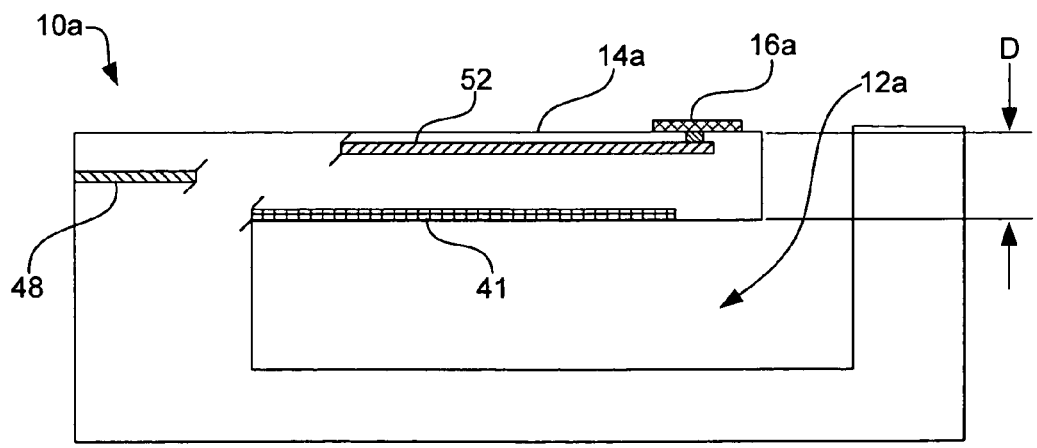
FIG. 3 is a front, sectional schematic view of the cantilever system shown formed in FIG. 2A through FIG. 2H and FIGS. 2J and 2K

Turning now to FIGS. 2K and 3, another embodiment of the present invention is shown in which the fluid actuator 16a is coupled to the flexible arm 14a. One exemplary process for forming this cantilever system is shown beginning in FIG. 2A, where a base material 40, such as a silicon wafer, is treated with various electronic elements 42 such as resistors, transistors, capacitors, etc. These various electronic elements can be selected based on the type of circuitry to be used in driving the cantilever of the system 10a and/or in detecting motion of the cantilever. Also, a resistive transducer, such as a piezoelectric sensor 41 can be attached to the base material to be used to detect movement of the flexible arm 14a (formed in later steps).

As shown in FIG. 2B, after the electronic elements (not shown in this FIG.) are deposited or defined on the base material, a layer of electrically insulating material 44a, such as a dielectric, can be applied over the base material 40 and the electronic elements to insulate the electric elements from contact with other elements and with the fluid in which the cantilever system will be used. Suitable openings 46 can be left or etched in the dielectric material to provide electrical contact with the electronic elements. The openings 46 can be filled with metal or other electrically conducting material to form "posts" through which electrical contact can be made through the dielectric layer 44a to the electronic components.

As shown in FIG. 2C, a layer including conductive strips 48, which can be formed of metal or another electrically conducting material, can be applied over the electrically insulating material 44a to provide paths for the conduction of electricity to and from the various electronic elements (shown in FIG. 2A). An additional layer of electrically insulating material 44b can be formed around the conductive strips. As shown in FIG. 2D, another layer of electrically insulating material 44c can be applied to the system, with one or more openings 45 left exposed to interconnect one or more of the paths provided by conductive strips (shown in FIG. 2C). As shown in FIGS. 2E and 2F, another series of conductive strips 52 can be created, within additional layer of electrically insulating material 44d, after which an additional layer of dielectric material 44e can be applied, with two openings 56 remaining exposed for connection to the conductive strips 52 established in FIG. 2E.

In FIG. 2G, a fluid actuator 16a can be coupled through the openings 56 (shown in FIG. 2F) to the conductive strips 52 (shown in FIG. 2E). In this manner, a fluid actuator, as well as the circuitry used to actuate the fluid actuator, and the circuitry used to detect movement of the flexible arm (not yet formed) are integrated and incorporated into a substantially solid block of material. Thus, an integrated, micro-electro-mechanical sensing system can be provided that can be used in a variety of fluid mediums, including liquid mediums.

FIGS. 2H, 2J, and 2K illustrate removal of portions of the base structure and layers added during construction of the cantilever system to define flexible arm 14a and fluid channel 12a. The resulting product, shown in sectional view in FIG. 3, can be coupled to a power source and a data collection system (neither shown in the figures) for use in a variety of testing regimes. As shown in FIG. 3, in one aspect of the invention, the piezoelectric sensor 41 can be disposed within the flexible arm at a position vertically (as referenced in the figures) offset from the center of the arm. In this manner, the sensor is offset from the neutral axis of the cantilever or flexible arm.

Cantilever systems in accordance with the present invention can be used in a variety of applications and can accordingly be provided in a variety of sizes and configuration. In one aspect of the invention, however, the cantilever systems can be incorporated into microfluidic systems to sense properties of fluids on a micro scale. In these embodiments, a fluid channel can comprise a micro-fluid channel and the flexible arm can comprise a micro-cantilever. Thus, in the embodiment illustrated in FIGS. 2K and 3, the flexible arm or cantilever 16a can include a length "L" on the order of 1500 µm, a width "W" on the order of 500 µm, and a depth "D" on the order of 500 µm. It is to be understood, however, that the present invention is not limited by the previously provided dimensions, but can be configured in a variety of sizes, on both a macro and a micro scale.

In addition to the features discussed above, the present invention also provides a method for forming a cantilever system for use in determining a property of a fluid, comprising the steps of forming a polymeric flexible arm and disposing a fluid actuator proximate to and spaced from the polymeric flexible arm, wherein the polymeric flexible arm and the fluid actuator are sufficiently close in proximity that actuation of the fluid actuator in the presence of the fluid induces movement of the polymeric flexible arm.

In addition, the present invention also provides a system for sensing a property of a fluid, including a fluid channel operable to receive the fluid therein. A flexible arm can have a free end positioned within at least a portion of the fluid channel. Means for actuating the fluid to induce movement of the flexible arm when the fluid is present can be disposed sufficiently close to the flexible arm. The means for actuating the fluid can include the fluid actuators discussed above. Means for sensing deflection of the flexible arm to quantify movement of the flexible arm can be operably coupled to the flexible arm and the actuation means.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A system for sensing a property of a fluid, comprising:
   a fluid channel operable to receive the fluid therein;
   a flexible arm having a free end positioned within at least a portion of the fluid channel;
   a fluid actuator disposed sufficiently close to the flexible arm such that actuation of the fluid actuator induces movement of the flexible arm when the fluid is present; and
   a deflection sensing system operable to quantifiably detect movement of the flexible arm.

2. The system of claim 1, wherein the flexible arm includes a section that is at least partially functionalized to absorb and/or react with an analyte in the fluid to determine a property of the fluid.

3. The system of claim 1, wherein the fluid is a liquid.

4. The system of claim 1, wherein the fluid actuator comprises an acoustic actuator.

5. The system of claim 1, wherein the fluid actuator comprises a thermal ink-jet-type actuator.

6. The system of claim 1, wherein the fluid actuator is disposed proximate to and spaced from the flexible arm.

7. The system of claim 1, wherein the fluid actuator is disposed on the flexible arm.

8. The system of claim 1, wherein the flexible arm is comprised of a polymer.

9. The system of claim 1, wherein the sensing system includes a piezoelectric sensor in operable communication with the flexible arm.

10. The system of claim 1, wherein the fluid channel comprises a micro-fluid channel and wherein the flexible arm comprises a micro-cantilever.

11. A method for forming a cantilever system for use in determining a property of a fluid, comprising the steps of:
    forming a polymeric flexible arm; and
    disposing a fluid actuator proximate to and spaced from the polymeric flexible arm, wherein the polymeric flexible arm and the fluid actuator are sufficiently close in proximity that actuation of the fluid actuator in the presence of the fluid induces movement of the polymeric flexible arm.

12. The method of claim 10, wherein the step of forming the polymeric flexible arm includes the steps of:
    forming a layer of removable support material;
    disposing a layer of polymer over the layer of removable support material; and
    removing the removable support material to enable movement of the polymeric flexible arm.

13. The method of claim 11, comprising the further step of functionalizing the polymeric flexible arm by depositing a reactant chemical on at least a portion of the polymeric flexible arm.

14. The method of claim 11, wherein the fluid actuator comprises an acoustic actuator.

15. The method of claim 11, wherein the fluid actuator comprises a thermal ink-jet actuator.

16. The method of claim 11, comprising the further step of incorporating the polymeric flexible arm and the fluid actuator within a deflection sensing system operable to quantifiably detect movement of the polymeric flexible arm.

17. The method of claim 16, wherein the deflection sensing system includes a piezoelectric sensor in operable communication with the polymeric flexible arm to quantifiably detect movement of the flexible arm.

18. The method of claim 16, wherein the flexible arm comprises a micro-cantilever.

19. A method for forming an integrated micro-electromechanical sensing system for use in a fluid, comprising the steps of:
    forming a flexible arm of the sensing system, the flexible arm including at least two connector strips of electrically conducting material; and
    coupling a fluid actuator to the flexible arm and to at least a portion of each of the two connector strips of electrically conducting material, the fluid actuator operable to induce movement in the deflectable arm upon actuation of the fluid actuator.

20. The method of claim 19, comprising the further step of functionalizing the flexible arm by depositing a reactant chemical on at least a portion of the flexible arm.

21. The method of claim 19, wherein the fluid actuator comprises an acoustic actuator.

22. The method of claim 19, wherein the fluid actuator comprises a thermal ink-jet actuator.

23. The method of claim 19, comprising the further step of incorporating the flexible arm and the fluid actuator within a deflection sensing system operable to quantifiably detect movement of the flexible arm.

24. The method of claim 23, wherein the deflection sensing system includes a piezoelectric sensor in operable communication with the flexible arm to quantifiably detect movement of the flexible arm.

25. The method of claim 23, wherein the deflection sensing system includes an optical sensor in operable communication with the flexible arm to quantifiably detect movement of the flexible arm.

26. A system for sensing a property of a fluid, comprising:
a fluid channel operable to receive the fluid therein;
a flexible arm having a free end positioned within at least a portion of the fluid channel;
means for actuating the fluid disposed sufficiently close to the flexible arm to induce movement of the flexible arm when the fluid is present; and
means for sensing deflection of the flexible arm to quantify movement of the flexible arm.

27. The system of claim 26, wherein the flexible arm includes a section that is at least partially functionalized to absorb and/or react with an analyte in the fluid to determine a property of the fluid.

28. The system of claim 26, wherein the means for actuating the fluid is disposed proximate to and spaced from the flexible arm.

29. The system of claim 26, wherein the means for actuating the fluid is disposed on the flexible arm.

30. The system of claim 26, wherein the flexible arm is comprised of a polymer.

* * * * *